United States Patent
Van Wyk et al.

(10) Patent No.: US 8,932,283 B2
(45) Date of Patent: Jan. 13, 2015

(54) CABLE ASSEMBLIES FOR ELECTROSURGICAL DEVICES AND METHODS OF USE

(71) Applicant: ElectroMedical Associates LLC, Bethesda, MD (US)

(72) Inventors: Robert A. Van Wyk, St. Pete Beach, FL (US); Yuval Carmel, Bethesda, MD (US); Anatoly Shkvarunets, Rockville, MD (US)

(73) Assignee: ElectroMedical Associates, LLC, Bethesda, MD (US)

( * ) Notice: Subject to any disclaimer, the term of this patent is extended or adjusted under 35 U.S.C. 154(b) by 0 days.

(21) Appl. No.: 13/762,848

(22) Filed: Feb. 8, 2013

(65) Prior Publication Data

US 2014/0088593 A1 Mar. 27, 2014

Related U.S. Application Data

(60) Provisional application No. 61/744,488, filed on Sep. 27, 2012, provisional application No. 61/795,832, filed on Oct. 29, 2012.

(51) Int. Cl.
*A61B 18/14* (2006.01)
*A61B 18/16* (2006.01)
*A61B 18/12* (2006.01)
*A61B 18/00* (2006.01)

(52) U.S. Cl.
CPC ....... *A61B 18/16* (2013.01); *A61B 2018/00625* (2013.01); *A61B 2018/00178* (2013.01); *A61B 2018/00601* (2013.01); *A61B 18/12* (2013.01); *A61B 18/1402* (2013.01)
USPC ............................................. 606/34; 606/48

(58) Field of Classification Search
USPC ............................ 606/32–34, 38–41, 48–50
See application file for complete search history.

(56) References Cited

U.S. PATENT DOCUMENTS

| | | | | |
|---|---|---|---|---|
| 4,427,006 A | | 1/1984 | Nottke | |
| 5,472,442 A | * | 12/1995 | Klicek | ............................ 606/42 |
| 5,573,424 A | * | 11/1996 | Poppe | ........................... 439/502 |
| 5,633,578 A | | 5/1997 | Eggers et al. | |
| 5,944,646 A | | 8/1999 | Weder et al. | |
| 6,113,596 A | * | 9/2000 | Hooven et al. | ................... 606/42 |
| 6,149,646 A | | 11/2000 | West et al. | |
| 6,823,218 B2 | | 11/2004 | Berube | |
| 6,840,937 B2 | | 1/2005 | Van Wyk | |
| 6,949,096 B2 | | 9/2005 | Davison | |
| 7,563,261 B2 | | 7/2009 | Carmel et al. | |
| 7,566,333 B2 | | 7/2009 | Van Wyk et al. | |
| 7,611,509 B2 | | 11/2009 | Van Wyk | |
| 7,909,820 B2 | * | 3/2011 | Lipson et al. | ................... 606/34 |
| 8,308,724 B2 | | 11/2012 | Carmel et al. | |
| 8,613,627 B2 | * | 12/2013 | Selig et al. | .................... 439/222 |

(Continued)

*Primary Examiner* — Michael Peffley
(74) *Attorney, Agent, or Firm* — Chalin A. Smith; Smith Patent

(57) ABSTRACT

Herein described is a novel cable assembly that is free from additional resistor, capacitor and inductor components and suitable for connecting a bipolar device to the monopolar active and return receptacles of a standard multipurpose electrosurgical generator. The cable assembly of the instant invention uses a conventional connector currently in use for either hand or foot control of electrosurgical pencils and a standard connector currently in use for dispersive electrodes; either single-foil (solid) or dual-foil (split) configuration connectors may be used. No resistors, capacitors, inductors transformers, or interface circuitry are incorporated in the cable or connectors distal to the electrosurgical generator.

13 Claims, 14 Drawing Sheets

(56) References Cited

U.S. PATENT DOCUMENTS

| | | |
|---|---|---|
| 2004/0030330 A1* | 2/2004 | Brassell et al. .................. 606/41 |
| 2006/0235377 A1 | 10/2006 | Earley et al. |
| 2006/0293653 A1 | 12/2006 | Van Wyk |
| 2007/0016182 A1 | 1/2007 | Lipson et al. |
| 2010/0324550 A1 | 12/2010 | Morgan et al. |
| 2011/0264092 A1 | 10/2011 | Van Wyk |
| 2011/0282341 A1 | 11/2011 | Carmel et al. |
| 2012/0095457 A1* | 4/2012 | Morgan et al. .................. 606/34 |

* cited by examiner

CABLE ASSEMBLIES FOR ELECTROSURGICAL DEVICES AND METHODS OF USE

PRIORITY

This application claims the benefit of U.S. Provisional Application Ser. No. 61/744,488 filed Sep. 27, 2012 and U.S. Provisional Application Ser. No. 61/795,832 filed Oct. 29, 2012, the entire contents of which are incorporated by reference herein.

FIELD OF THE INVENTION

This invention relates to electrosurgical devices designed for use with a general-purpose electrosurgical generator and more specifically to a device and method for increasing the cutting and vaporizing efficiency of bipolar electrosurgical devices characterized by a return electrode in close proximity to the active electrode when such devices are used with a general-purpose generator.

BACKGROUND OF THE INVENTION

The popularity of electrosurgical techniques and devices has grown dramatically due to their ability to cut, coagulate and vaporize tissue. In one aspect, highly specialized devices for unique, highly-focused applications requiring precise control have been developed and continue to proliferate. In a second aspect, general-purpose electrosurgical systems and devices have been developed which can be produced at low cost and may be used for a wide variety of surgical applications. Over the years, electrosurgical generators frequently referred to as "general-purpose" generators have been developed; by design, these generators are meant to be highly generic and therefore find universal application. Typical of these generators are the IDS-200, IDS-300 and IDS-400 generators by Bovie Medical Corporation (Clearwater, Fla.), the System 5000 and System 2450 generators by Conmed, Incorporated (Utica, N.Y.), the ICC-300, ICC350 and VIO by Erbe (Tubingen, Germany) and the Force FX and Force EZ generators by Valleylab/Covidien, Inc (Colorado Springs, Colo.). These general-purpose generators may have power levels up to 400 Watts when used in monopolar mode, and tend to be equipped with connectors for hand-controlled and foot-controlled operation of such monopolar devices. They are also provided with a separate connector for a monopolar patient return electrode, either a pad or plate style. These general-purpose generators also tend to have a separate bipolar connector for connecting devices such as bipolar coagulating forceps. These bipolar outputs are generally limited to 80 Watts, this power level being sufficient for cautery applications. The connectors of the generators are sometimes also referred to as receptacles, sockets, output connectors or jacks.

The devices designed for use with these general-purpose generators have been largely commoditized. Monopolar devices generally referred to as "electrosurgical pencils" from many manufacturers can be used with generators from many others. Such an electrosurgical pencil is described by Nottke in U.S. Pat. No. 4,427,006. A variety of electrosurgical electrodes may be removably mounted to such devices to accomplish a wide range of medical tasks. The pencils may be either hand- or foot-controlled. Foot-controlled devices tend to include a single-wire electrical power cord that is connected to a "foot pedal" monopolar receptacle on the front panel of a general-purpose generator. Hand-controlled, sometimes referred to as finger-controlled, pencils, tend to use a three-wire power cord that terminates at its proximal end with a linear three-pin connector (also referred to as 3-prong connector or plug), which then connects to the "hand-controlled" monopolar receptacle on the front panel of the generator. The three pin connector of electrosurgical pencils and three pin receptacle on the general-purpose generators have been sufficiently standardized to allow interchangeability between devices and generators produced by many companies, particularly in the U.S.

The interface between the monopolar patient return electrode and the generator has been similarly standardized. The size, configuration and materials of return electrodes and plates vary widely; however, all use a two-wire cord having a standard connector at the proximal end, the connector being configured to fit a mating standardized socket on the front panel of a general-purpose electrosurgical generator.

Devices for use with the generator bipolar output have also been commoditized, the devices being generally bipolar in the classical definition—having two electrodes that are symmetrical in size and shape. Typical of these are various kinds of bipolar coagulating forceps that grasp tissue between their jaws so that current flow is from one jaw to the other so as to desiccate the tissue. The power cords and power connectors for these devices are largely standardized such that the power cords and devices from many manufacturers can be used with generators produced by many other manufacturers. Operation of these bipolar devices is controlled by a foot-pedal. The bipolar generator output is configured for efficient control of bleeding through tissue desiccation while avoiding the sparking which causes tissue destruction. This is accomplished by the generator through limiting the available power, lower voltages, and using a suitable power curve suitable for coagulating tissue held between grasping bipolar jaws like those of bipolar coagulating forceps.

Because the bipolar output of a general-purpose generator is configured to minimize sparking, it is not well suited to use with devices having a return electrode on the device in close proximity to the active electrode and which are specifically designed to cut or vaporize tissue. Using the standard bipolar output of a general-purpose generator to power a device such as a "bipolar" arthroscopy ablator (one with a return electrode in close proximity to the active electrode) would result in extremely inefficient operation at best. Therefore, currently available arthroscopy ablators of this type are used with a dedicated (not general-purpose) generator having specialized output power characteristics and/or modulated waveforms. Examples of such dedicated bipolar radiofrequency generators for arthroscopy include the System 2000, Atlas and Coblator II by Arthrocare (Austin Tex.), SERFAS by Stryker (San Jose, Calif.), and VAPR by DePuy Mitek Inc (Raynham, Mass.). Dedicated bipolar generators are also available for other medical procedures.

Although general-purpose electrosurgical generators are available in every operating room, it is necessary to use a special purpose generator for return-in-close-proximity applications that primarily cut or vaporize tissue. Because the efficiency of cutting or vaporizing tissue with such a device when powered by the bipolar receptacle of a general-purpose generator is unacceptably low, there are not low-cost commoditized devices having a return electrode in close proximity on the device available for use with these general-purpose generators.

However, specialized dedicated equipment is not preferred in a hospital setting. Not only does the procurement and storage contribute to overhead costs, but, given that such specialized equipment tend to be less ubiquitous, additional transport and/or scheduling is often necessitated. To address this problem, attempts have been made to connect bipolar devices to the monopolar outputs of standard multipurpose electrosurgical generators. However, as discussed in detail below, all require either reconfiguration of or modification to the output signal (e.g., load curve, ablation curve, etc.) or the use of additional electrical components such as resistors, capacitors, inductors, transformers and/or other interface circuitry.

In U.S. Pat. No. 5,633,578, Eggers et al. teach the connection of haemostatic bipolar devices to the monopolar outputs of a standard multipurpose generator using conversion devices. The intent is to provide "adaptors for use with conventional electrosurgical generators to provide voltage output waveforms effective in reducing coagulum buildup, and to alleviate sticking, on hemostatic electrosurgical instruments". This is accomplished by the use of external, voltage-limiting circuitry for modifying the generator output waveforms in order to prevent arcing. However, the systems taught are not applicable to devices used for cutting and bulk vaporization since these require sparking, and decreasing the voltage decreases the efficiency of these devices to generate sparks.

In U.S. Patent Application Publication No. 2007/0016182, Lipson et al. teach the connection of fluid-assisted bipolar devices to the monopolar outputs of a general-purpose generator using an adaptor that modifies the power levels and load curves of the generator. Quoting Lipson, "[i]n order to reduce monopolar voltage and impedance ranges to desirable levels for bipolar use, a transformer may be placed in series circuit configuration between the electrodes of bipolar device 5i and the monopolar mode power output of the generator 6." The intent is to use circuitry distal to the generator to inhibit sparking caused by the high voltages present in monopolar outputs. Accordingly, the resulting RF power has inefficient characteristics for tissue vaporization. Again in U.S. Pat. No. 7,909,820 Lipson et al. teach the use of a transformer distal to the generator in order to change its characteristics, In U.S. Patent Application Publication No. 2004/0030330, Brassell et al. teach a bipolar device for rasping tissue while applying RF energy thereto, together with an adaptor with circuitry for connecting the device to the monopolar outputs of a general-purpose electrosurgical generator. Quoting Brassell, "[g]enerally, generator 32 provides constant electric power to adapter module 34, which converts the power to a form useable by probe 36, e.g., approximately constant voltage." and "Advantages of the invention may include . . . (v) minimizing the possibility of runaway current during electrosurgery by providing an adapter that converts constant power output from a generator to constant voltage output for an electrosurgical probe". Apparently this was a unique requirement for the disclosed bipolar device. To achieve these goals Brassell teach circuitry distal to the generator adapted to convert substantially constant power to constant voltage output.

In U.S. Pat. Application Publication No. 2012/0095457, Morgan et al. disclose a method for connecting a non-vaporizing bipolar device to the monopolar output on a standard generator through the use of "active components" connected between the output and return cabling of the generator, distal to the generator. The active components are used to match the impedance of the load to that of the generator. This matching allows the use of bipolar devices at low power levels. However, this performance is achieved by eliminating one of the wires connected to the standard three-pin hand-control monopolar output of the generator so that the bipolar device can operate only in one mode, either Cut only or Coag only. Thus, the operator is able to activate the device in the chosen waveform and power level, but does not have the ability to switch between waveforms and preset power levels for Cut and Coag functions. This can seriously limit the surgeon ability to deliver the optimal therapeutic effect to the patient. Furthermore, this approach requires adding external, non-standard bridging/balancing electrical components between the generator and the electrosurgical device in order to substantially mimic the load response produced by an external return circuit of a monopolar electrosurgical unit. Similarly, in U.S. Patent Application Publication No. 2010/0324550, Morgan et al. teach the use of a current bridge, distal to the generator, in order to change the generator characteristics by producing a matched impedance to a load condition. Morgan teaches away from vaporization.

While these various adaptors and adapting methods are suitable and necessary for their associated devices, their effect is to produce outputs with characteristics that are less suited to the vaporization of tissue than those of the standard un-modified monopolar output. Additionally, they add unnecessary complexity and cost if the outputs are to be used primarily for tissue vaporization and cutting. Adding external components and circuitry distal to the generator other than wires, and connecting or interconnecting components is outside the scope of this invention. The present invention herein disclosed addresses these and other problems by providing a novel cable assembly that is free from additional interface circuitry or electronic components, such as resistors, capacitors, inductors, and transformers, and suitable for connecting a bipolar device to the monopolar active and return receptacles of a standard multipurpose electrosurgical generator.

SUMMARY OF THE INVENTION

The present inventors have discovered that a device for tissue vaporization or cutting that includes a return electrode in close proximity to an active electrode such as, for instance, an arthroscopy ablator, can be efficiently operated using the power output of a general-purpose generator if means are provided for connecting the generator monopolar output and monopolar return to the device. In the context of the present invention, the active electrode of the device is connected via cabling and means within the device handle to a "monopolar" receptacle of a general-purpose generator, and the return electrode on the device is connected via cabling and means within the device handle to the "return" receptacle of the general-purpose generator.

More specifically, the inventors have discovered that it is possible to make a highly efficient, hand-controlled, ablation device with the return on the device in close proximity to the active electrode by using cabling that connects activation buttons on the device handle and the ablator active electrode to the standard three-pin "hand-control" receptacle on a general-purpose generator, and by using cabling to connect the return electrode on the bipolar device to the "return" receptacle on the generator. This hand-controlled device allows hand activation of both the Cut and Coag functions, and compatibility with multiple general-purpose generators. It is also possible to construct a highly efficient foot-pedal controlled electrosurgical device by using cabling which connects the monopolar "foot-control" receptacle of the generator to the active electrode of the device, and which connects the return electrode on the bipolar device to the "return" receptacle on the generator. Electronic components such as capacitors, inductors, resistors, transformers, interface circuitry components or balancing bridges between the active and return means are expressly not required.

Comparative testing of a device constructed and operated in accordance with the principles of this invention, that is, with a return electrode in proximity to the active electrode and connected to the monopolar outputs of a standard electrosurgical generator, and the same device operated in standard monopolar mode with a remotely located return electrode show performance to be equivalent. Thus, contrary to expectations, the bipolar device operates according to the monopolar load curves of the electrosurgical general-purpose generator.

The invention herein disclosed may also be advantageously applied to true bipolar devices that are used for surface coagulation. Rather than the bipolar electrodes forming grasping jaws as in the bipolar forcep devices previously herein described, these surface coagulators have bipolar electrodes in the form of a pair of relatively large rounded elements spaced a fixed distance apart. Since the elements are configured to desiccate tissue using low current density RF power, they have no "sharp" features or surface irregularities that would cause regions of high current density. Because the exposed areas of the electrodes are large and the power may be additionally diffused by a supplied conductive irrigant, these devices are used with dedicated generator capable of producing up to 200 Watts of RF energy. The inventors have herein discovered that it is possible to efficiently power such devices using the monopolar output of a general-purpose electrosurgical generator in the same manner as the vaporizing and cutting devices previously described. Because the exposed areas of the electrodes are large and the electrodes have no features for increasing current density, the higher voltage and power of the monopolar output can be used without undesired sparking when the devices are used correctly, that is, not energized until the electrodes are in contact with the tissue, or irrigant or body fluids. Irrigating the surface with a conductive fluid during use prevents adhering of tissue to the electrodes and further diffuses the coagulating current.

Because the connectors have been standardized for general-purpose generators, using the invention herein disclosed it is possible to produce low-cost commoditized, high performance bipolar devices for use with the generators already present in every operating room, alleviating the need for specialized capital equipment. General-purpose electrosurgical generators are present in every operating room, and it is estimated that installed base of general-purpose electrosurgical generator is ten times larger than that of dedicated generators. By using the principles of this invention, patient safety will be enhanced by reducing scheduling conflicts in the operating room that may occur when the number of needed procedures exceeds the number of dedicated generators available at the facility. It is also possible, with a suitable adaptor, to connect existing vaporizing and cutting bipolar devices designed for use with a dedicated, special-purpose generator to the monopolar outputs of a standard electrosurgical generator.

The invention herein disclosed relates to cutting or vaporizing devices having a return electrode located in close proximity to an active electrode, that is, within preferably 10 mm of the active electrode, and mounted to the device such that movement of the active electrode causes corresponding movement of the return electrode (e.g., bipolar devices). It is accordingly an objective of this invention to produce a bipolar electrosurgical device that may be connected to the monopolar connectors of a standard electrosurgical generator.

It is also an objective of this invention to produce a bipolar electrosurgical device that may be connected to the monopolar receptacles of a standard electrosurgical generator of simple construction, without requiring external components such as capacitors, inductors, resistors, transformers, or interface circuitry between the active and return conductors.

It is further an objective of this invention to produce a bipolar electrosurgical device that may be connected to the monopolar connectors of a standard electrosurgical generator wherein the connectors are of the standard, universal, and/or conventional configurations.

It is additionally an objective of this invention to produce an adaptor for connecting a bipolar electrosurgical device designed for use with a special-purpose generator to the monopolar connectors of a standard electrosurgical generator.

It is further an objective of this invention to produce a bipolar electrosurgical device which may be connected to the monopolar connectors of a standard electrosurgical generator wherein the device has hand activations for both cut and coag generator functions.

It is yet another objective of this invention to allow for compatibility between various types of bipolar devices with multiple types of general-purpose electrosurgical radiofrequency generators.

It is yet a further objective of this invention to improve patient safety by reducing scheduling conflicts in the operating room that may occur when the number of needed procedures exceeds the number of dedicated electrosurgical generators available at the facility.

It is also an objective of this invention to substantially reduce the cost of various medical procedures by eliminating the need for investing in specialized capital equipment when electrosurgical devices having the return electrode(s) located on the device in close proximity to the active electrode(s) are used by allowing their use in conjunction with a general-purpose generator.

It is a further objective of this invention to allow for operation in wet (conductive or non conductive) and semi dry fields/bodily fluid environment.

It is yet another objective of this invention to allow for compatibility with suction and irrigation when needed.

Finally, it is an objective of this invention to produce a bipolar electrosurgical device which may be connected to the monopolar connectors of a standard electrosurgical generator wherein the device may be activated in cut or coag mode using foot-pedals.

These and other objects are accomplished in the invention herein disclosed, It will be understood by those skilled in the art that one or more aspects of this invention can meet certain of the above objectives, while one or more other aspects can meet certain other objectives. Each objective may not apply equally, in all its respects, to every aspect of this invention. As such, the preceding and foregoing objects should be viewed in the alternative with respect to any one aspect of this invention.

A first aspect of the invention herein described relates to an electrosurgical device having a return electrode mounted in proximity to an active electrode such that movement of the active electrode causes corresponding movement of the return electrode, and with cabling connecting the active electrode to a monopolar output connector of a standard general-purpose electrosurgical generator, and connecting the return electrode of the device to the monopolar return connector of the generator. According to the principles of this invention, the connections are made using the standard universal connector configurations common to existing monopolar commodity electrosurgical devices such as electrosurgical pencils and patient return (dispersive) pads. Additionally, the bipolar device may have buttons for activating the generator Cut and Coag functions, the buttons connected to the generator via cabling connected to the standard three-pin "hand control"

connector on a standard electrosurgical generator. Alternatively, the active electrode may be connected to the generator via the "foot control" connector and the Cut and Coag functions activated using standard foot-pedals attached to the generator in the usual manner.

Current bipolar devices for tissue vaporization or cutting are used with special-purpose generators that connect to the devices using special cabling having multiple wires and multi-pin connectors. Accordingly, a second aspect of the invention herein disclosed relates to an adaptor for connecting the multi-pin connectors of these bipolar devices to the standard monopolar outputs of a standard multipurpose electrosurgical generator. The multiple wires of the device may have various functions related to device identification by the generator, hand activation, and connection to the active and return electrodes. The adaptor of the present invention connects to the active and return connector pins, and may optionally connect to hand-control pins so as to allow hand-control of the generator Cut and Coag functions. In the absence of hand-controls on the device, or the absence of connections to existing hand-controls, the device is controlled by foot-pedals connected to the multi-purpose generator in the usual manner.

A third aspect of the invention herein disclosed relates to a method for cutting, vaporizing or coagulating tissue using a bipolar device using the un-modified monopolar outputs of a standard multi-purpose electrosurgical generator.

The above-noted objects, aspects and features of the invention will become more fully apparent when the following detailed description is read in conjunction with the accompanying figures and/or examples. However, it is to be understood that both the foregoing summary of the invention and the following detailed description are of preferred embodiments and not restrictive of the invention or other alternate embodiments of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art having knowledge of electrode design. Such objects, features, benefits and advantages apparent from the above in conjunction with the accompanying examples, data, figures and all reasonable inferences to be drawn therefrom are specifically incorporated herein.

BRIEF DESCRIPTION OF THE FIGURES

Various aspects and applications of the present invention will become apparent to the skilled artisan upon consideration of the brief description of the figures and the detailed description of the present invention and its preferred embodiments that follows:

FIG. 1(*b*) is a schematic representation of the connector portion of the prior art electrosurgical generator of FIG. 1.

FIG. 2(*b*) depicts a prior art monopolar return connector for a dual-foil pad.

DESCRIPTION OF THE PREFERRED EMBODIMENTS

Figure 1A:
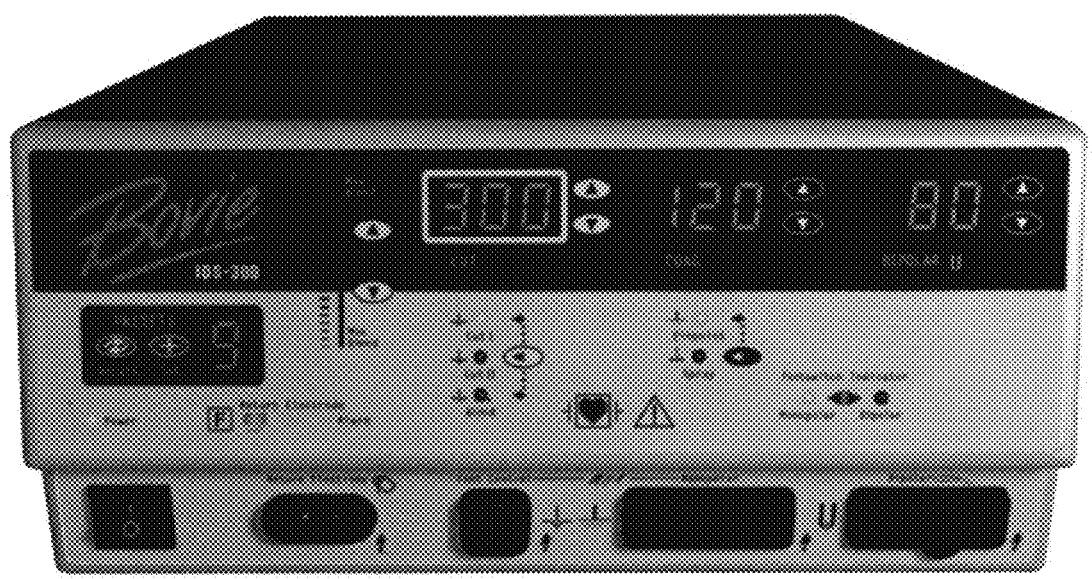
FIG. 1(*a*) depicts a prior art general-purpose electrosurgical generator.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Elements of the Present Invention:

Unless otherwise defined, all technical and scientific terms used herein have the same meaning as commonly understood by one of ordinary skill in the art to which this invention belongs. In case of conflict, the present specification, including following definitions, will control.

The words "a", "an", and "the" as used herein mean "at least one" unless otherwise specifically indicated.

The term "proximal" refers to that end or portion which is situated closest to the user; in other words, the proximal end of a component or cable of the instant invention will typically include a first connector adapted to connect with a receptacle or socket on the general-purpose generator.

The term "distal" refers to that end or portion situated farthest away from the user; in other words, the distal end of a component or cable of the instant invention will typically include a second connector adapted to connect with a receptacle or socket disposed on the handle portion of the electrosurgical device.

The present invention makes references to various cabling connections. In the context of the instant invention, the terms "receptacle" and "socket" are used interchangeably to refer to a recessed female connector adapted to connect with a mating male counterpart. In the context of the present invention, this mating male counterpart is referred to interchangeably as a "connector", a "male connector", and a "plug". The present invention makes use of conventional male-female connectors that are standard in the electrosurgical arts, including, but not limited to, the linear single-pin and three-pin connectors (also referred to as 1- and 3-prong connectors and 1- and 3-prong plugs).

In certain embodiments, the present invention makes reference to "fluid(s)". As used herein, the term "fluid(s)" refers to liquid(s), either electrically conductive or non-conductive, and to gaseous material, or a combination of liquid(s) and gas(es). In the context of the present invention, the term "fluid" extends to body fluids, examples of which include, but not limited to, blood, peritoneal fluid, lymph fluid, pleural fluid, gastric fluid, bile, and urine.

The present invention makes reference to the ablation, coagulation and vaporization of tissue. As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. The present invention is not limited in terms of the tissue to be treated but rather has broad application, including the resection and/or vaporization any target tissue with particular applicability to the ablation, destruction and removal of problematic joint tissues.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

In common terminology and as used herein, the term "electrode" may refer to one or more components of an electrosurgical device (such as an active electrode or a return electrode) or to the entire device, as in an "ablator electrode" or "cutting electrode". Such electrosurgical devices are often interchangeably referred to herein as "probes", "devices" or "instruments".

Electrosurgical devices contemplated by the present invention may be fabricated in a variety of sizes and shapes to optimize performance in a particular surgical procedure. For instance, devices configured for use in small joints may be highly miniaturized while those adapted for shoulder, knee and other large joint use may need to be larger to allow high rates of tissue removable. Likewise, electrosurgical devices for use in arthroscopy, otolaryngology and similar fields may be produced with a rounded geometry, e.g., circular, cylindrical, elliptical and/or spherical, using turning and machining processes, while such geometries may not be suitable for other applications. Accordingly, the geometry (i.e., profile, perimeter, surface, area, etc.) may be square, rectangular, polygonal or have an irregular shape to suit a specific need.

The present invention makes reference to one or more "active electrodes" or "active elements". As used herein, the term "active electrode" refers to one or more conductive elements formed from any suitable preferably spark-resistant metal material, such as stainless steel, nickel, titanium, molybdenum, tungsten, and the like as well as combinations thereof, connected, for example via cabling disposed within the elongated proximal portion of the instrument, to a power supply, for example, an externally disposed electrosurgical generator, and capable of generating an electric field. Like the overall electrosurgical device, the size, shape and orientation of the active electrode itself and the active surface (i.e., ablating surface) defined thereby may routinely vary in accordance with the need in the art. It will be understood that certain geometries may be better suited to certain utilities. Accordingly, those skilled in the art may routinely select one shape over another in order to optimize performance for specific surgical procedures. For example, for accessing narrow structures like vertebral discs it may be desirable to use an elongated electrode of a narrow geometry, e.g., having a relatively flat profile. Thus, for the most part, choices in geometry constitute a design preference.

In certain embodiments, the present invention makes reference to one or more "return electrodes". As used herein, the term "return electrode" refers to one or more powered conductive elements to which current flows after passing from the active electrode(s) back to the general-purpose generator. This return electrode may be located on the electrosurgical device and may be formed from any suitable electrically conductive material, for example a metal material such as stainless steel, nickel, titanium, molybdenum, tungsten, aluminum and the like as well as combinations thereof.

The present invention makes reference to "insulators". This term is herein to refer to the non-conductive dielectric component that surrounds a distal end active electrode, covering all exposed surfaces of the active electrode with the exception of the electrically active surface (i.e., the ablating surface) that generally protrudes beyond the insulator a short distance. Accordingly, the geometry of the insulator is largely dictated by the geometry of the associated active electrode, which, as noted above, is not particularly limited. For example, the use of a substantially circular or cylindrical active electrode dictates the use of a largely tubular insulator sleeve. However, as with the overall electrosurgical device and active electrode itself, the size and shape of the insulator may routinely vary in accordance with the need in the art. It will be understood by those skilled in the art that such choices in geometry constitute a design preference and that other geometries may be used to optimize performance for specific surgical procedures.

Utilities of the Present Invention:

As noted above, the present invention is directed to electrosurgical devices and methods that employ high frequency voltage to cut, ablate and/or coagulate tissue, particularly joint tissue, in conductive fluid and semi-dry environments. However, as noted previously, the present invention is not restricted to arthroscopics. Aspects are equally applicable to other uses, for example in connection with reconstructive, cosmetic, oncological, ENT, urological, gynecological, and laparoscopic procedures, as well as in the context of general open surgery.

While some embodiments of the present invention are designed to operate in dry or semi-dry environments, others utilize the endogenous fluid of a "wet field" environment to transmit current to target sites. Still others require the use of an exogenous irrigant. In certain embodiments, the "irrigant" (whether native or externally applied) is heated to the boiling point, whereby thermal tissue treatment arises through direct contact with either the boiling liquid itself or steam associated therewith. This thermal treatment may include desiccation to stop bleeding (hemostasis), and/or shrinking, denaturing, or enclosing of tissues for the purpose of volumetric reduction (as in the soft palate to reduce snoring) or to prevent aberrant growth of tissue, for instance, endometrial tissue or malignant tumors. However, the present invention is not particularly limited to the treatment of any one specific disease, body part or organ or the removal of any one specific type of tissue, the components and instruments of the present invention.

Liquids (either electrically conductive or non-conductive) and gaseous irrigants, either singly or in combination may also be advantageously applied to devices for incremental vaporization of tissue. Normal saline solution may be used. Alternatively, the use of low-conductivity irrigants such as water or gaseous irrigants or a combination of the two allows increased control of the electrosurgical environment.

The electrosurgical devices of the present invention may be used in conjunction with existing diagnostic and imaging technologies, for example imaging systems including, but not limited to, MRI, CT, PET, x-ray, fluoroscopic, thermographic, photo-acoustic, ultrasonic and gamma camera and ultrasound systems. Such imaging technology may be used to monitor the introduction and operation of the instruments of the present invention. For example, existing imaging systems may be used to determine location of target tissue, to confirm accuracy of instrument positioning, to assess the degree of tissue vaporization (e.g., sufficiency of tissue removal), to determine if subsequent procedures are required (e.g., thermal treatment such as coagulation and/or cauterization of tissue adjacent to the target tissue and/or surgical site), and to assist in the traumatic removal of the device.

Illustrative Embodiments of the Present Invention

General-purpose electrosurgical generators are present in every operating room. These generators are advanced devices capable of efficiently performing a myriad of tasks in all types of surgery. They offer the user a variety of wave forms for cutting, coagulation and fulguration and also allow output power selections up to 400 watts. General-purpose generators are most commonly used with a monopolar electrosurgical pencil—a handle into which a variety of electrode shapes can be removably mounted. These electrodes may be blades, needles or wire loops for cutting tissue, or spherical shaped for coagulating bleeding surfaces. The current path through the patient is completed by a dispersive return electrode removably mounted on the patient at a site remote from the surgery site. Additionally, many of the generators have a bipolar output socket for powering coagulating devices such as forceps in which the current path is through tissue between a pair of electrodes so that no dispersive pad is required.

As noted above, the present invention affords a marked simplification as well as a universality to the use of bipolar electrosurgical devices. Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

Figure 1B:
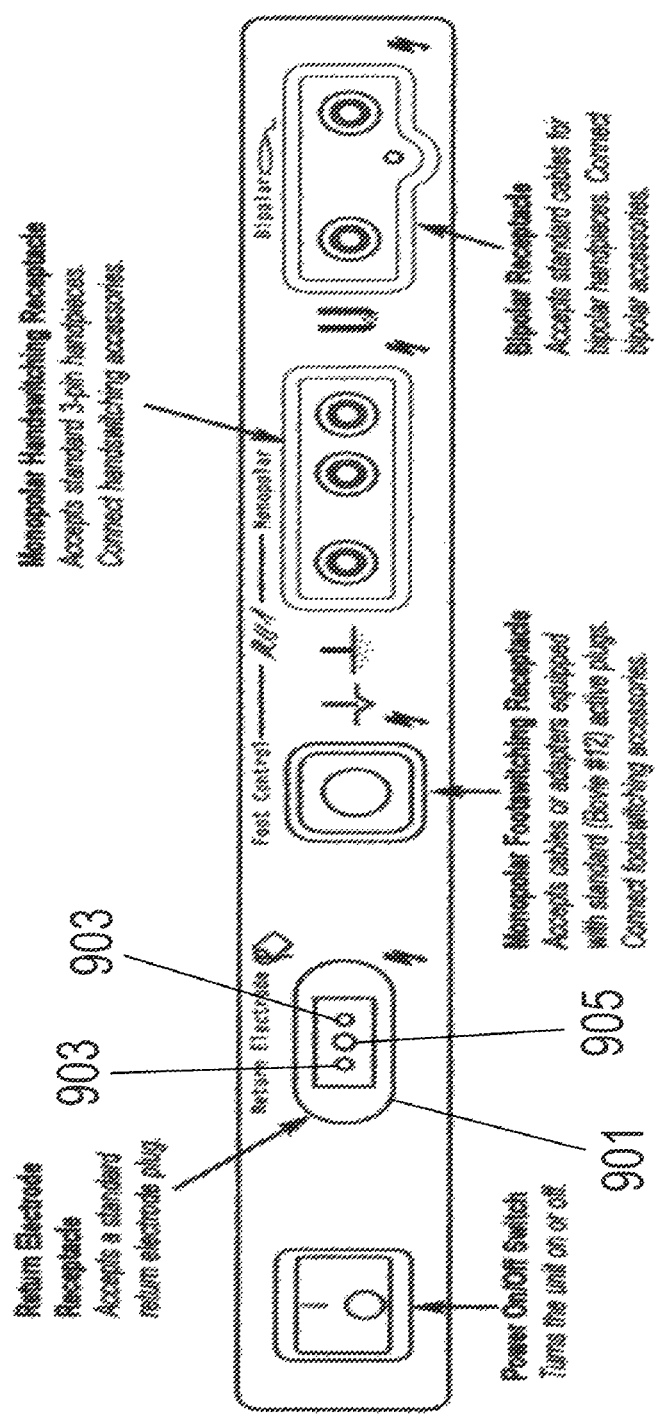

FIG. 1(a) depicts a typical prior art general-purpose electrosurgical generator, the IDS-300 sold by Bovie Medical, Inc. FIG. 1(b) is a schematic view of the connector portion of the front panel of this generator. Of particular interest are the various female connectors (or "sockets" or "receptacles"), with their descriptive notations; the bipolar receptacle, monopolar hand switching receptacle, monopolar foot switching receptacle, and return electrode receptacle each are described as usable with their respective "standard" male counterparts. This standardization of connectors and of the general operating characteristics of the generators of different manufacturers allows third-parties to produce both commodity and specialized devices for use with these generators. Accordingly, there has been a substantial proliferation of uniquely configured electrodes that may be mounted in a standard monopolar pencil. Also, there are now monopolar devices which are not pencils, but which use the same handactivation as standard pencils and thus are connected to the standard three-pin receptacle on a general-purpose generator. Exemplary of these are the OPES arthroscopy ablators sold by Arthrex, Incorporated (Naples, Fla.). All such hand-controlled devices are monopolar since current general-purpose generators do not have a means for hand-control of bipolar devices. Additionally, while the bipolar output of the generalpurpose generators is well suited to coagulation, because of the reduced maximum power level, and power curve suitable to avoid sparking, the bipolar output of general-purpose generators is not well suited to cutting or bulk vaporization of tissue through spark discharge.

These limitations have been overcome with the invention herein described, which is a device and method for operating a bipolar cutting or bulk vaporization device using the unmodified output of a general-purpose electrosurgical generator. Specifically, the bipolar device is connected via cabling to the monopolar output and return of the generator.

Figure 2A:
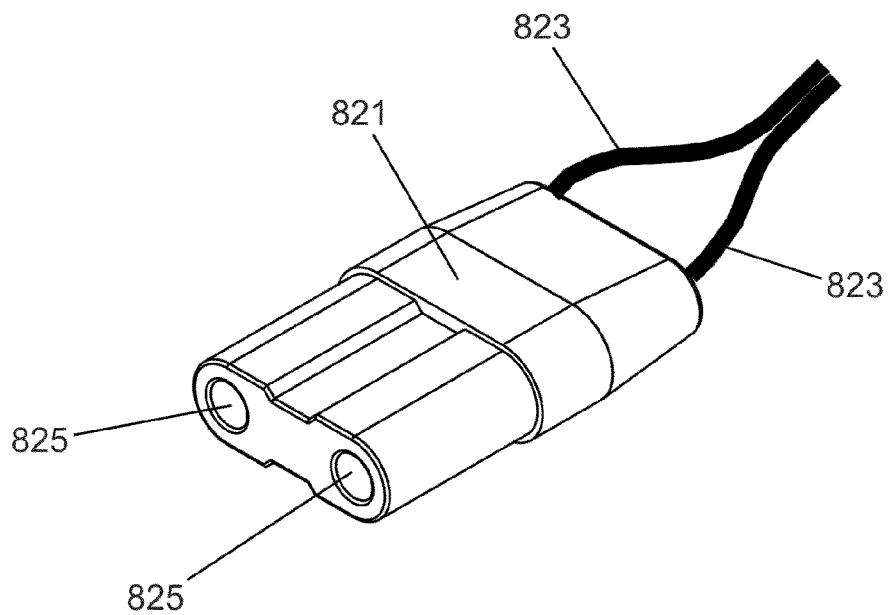
FIG. 2(*a*) depicts a prior art monopolar return connector for a single-foil pad.
Figure 2B:
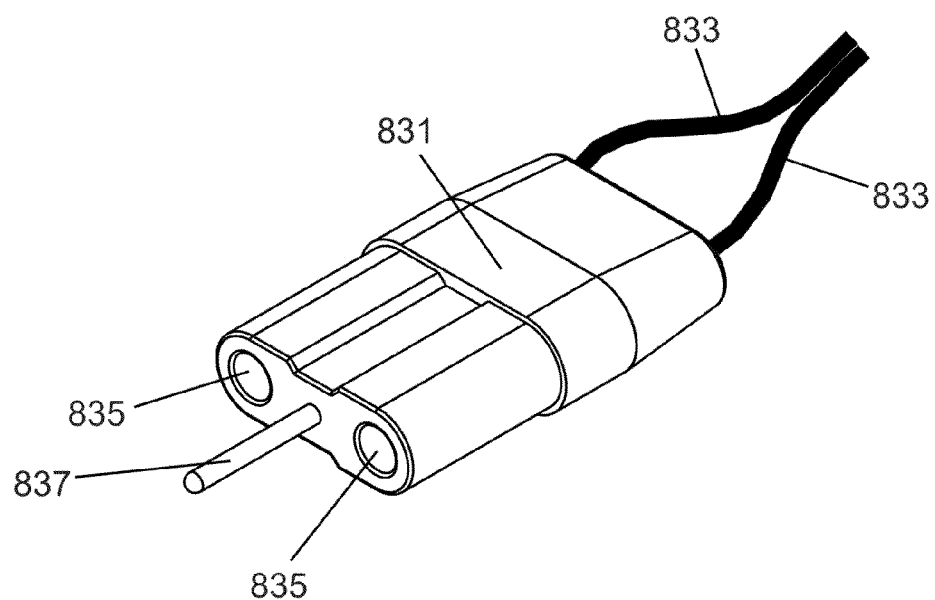

Referring again to FIG. 1(b) depicting a schematic view of the connector portion of the front panel of the generator, "Return Electrode Receptacle" 901 shows three linearly arranged circles, the outer two 903 having a common smaller diameter are protruding pins, the center circle 905 representing a hole in the front panel receptacle. Two types of return pads (also referred to as dispersive, or patient return electrodes) are commonly available. The first (commonly referred to as a "single foil" or "solid" pad) has two wires connected to a single conductive portion that is affixed to the patient's body. Examples of pads of this type are the "ESRSC solid adult return electrode w/2.8 M cable" by Bovie Medical, Inc. and MacroLyte REF 400-2100 by ConMed Corp. (Utica, N.Y.). Referring to FIG. 2(a), pads of this type have a standard connector like connector 821, the two wires 823 connecting to the connector conductors 825 so as to electrically connect to the pins of the Return Electrode Receptacle. During a medical procedure during which electrosurgical devices are used it may be possible for the return pad to become partially detached or disconnected from the patient due to improper application or other factors. In such cases, as the area of the pad in contact with the patient decreases, the current density of the portion of the pad in contact with the patient increases. This increased current density may burn the patient. Accordingly, a second type of pad, and monitoring circuitry within electrosurgical generators were developed to detect detachment of the return pad from the patient. This second type of pad (commonly referred to as a "dual foil" or "split" pad) has two conductive portions that are affixed to a patient's body. Examples of pads of this type are the "ESREC split adult return electrode w/2.8 M cable" by Bovie Medical, Inc. and REM PolyHesive II by Valleylab (now Covidien). Referring to FIG. 2(b), pads of this type have a standard connector like connector 831, the two wires 833 connecting to the connector conductors 835 so as to electrically connect to the pins of the Return Electrode receptacle. Connector 831 additionally has cylindrical protrusion 837 centrally positioned so that when connector 831 is inserted into the Return Electrode Receptacle 901 (FIG. 1(b)) protrusion 837 protrudes into the generator case via opening 905 (FIG. 1(b)). The presence of protrusion 837 indicates to the generator that the return pad is a dual foil type pad. The return electrode monitoring circuitry of the generator then senses the electrical conditions between the proximal end of the wires to establish that the electrical resistance is within the limits indicating that the pad is properly applied to and in contact with the patient. The generator then continues to monitor this resistance for changes that would indicate that the pad is losing its proper contact with the patient. Any change in the resistance beyond predetermined limits will cause the generator to shut down and alert the operator so as to prevent burning of the patient.

If a bipolar electrosurgical device is to be connected to a general-purpose generator using a split pad connector as taught by Morgan et al in U.S. application 2012/0095457, it is essential that the return electrode monitoring circuitry of the generator be "fooled" into sensing that a split pad is properly connected to the patient's body, and that the electrical conditions are within proper limits, otherwise the generator can not be activated. In order to achieve these goals, Morgan teaches adding electrical components distal to the generator, composed of resistors, capacitors and inductors. Morgan teaches that these additional electrical components are physically located in the handpiece of the electrosurgical device, or in the split pad connector, or in a separate external interface box. However, as noted above, the present invention expressly excludes adding such external components and circuitry other than electrical wires or connecting components for transmitting power to the bipolar device.

Standard multi-purpose electrosurgical generators also monitor the resistance between the two conductors 825 of single-foil pads with connectors 821 (FIG. 2(a)). Wires connected to conductors 825 extend to the return pad where they are electrically connected at their distal ends by the pad. If one of the connecting wires is broken or disconnected from the pad, the resistance is beyond the acceptable limits of the generator and operation of the generator is prevented. In this manner the integrity of the return circuit is ensured.

The inventors have discovered that if the standard electrical wires of a dual-foil pad are electrically connected together (shorted) at their distal end (at the pad) electrosurgical generators will operate even in the absence of a pad, the resistance of the wires being within the limits which the monitoring circuit of the generator requires for operation. This is not the case if the wires are shorted together at their proximal end (at or within the connector) since under these conditions the resistance will be below the acceptable range of the generator monitoring circuit unless additional components are added as taught by Morgan et al.

Furthermore, the inventors have also discovered that electrically connecting the wires of a single-foil pad together at their distal end will also create the proper conditions for the general-purpose generator to operate. In other words, the proper conditions for operation of a general-purpose generator can be created for both single and split pad standard connectors without adding external components and circuitry distal to the generator other than wires or serially connected wire segments. Specifically, this excludes resistors, capacitors, inductors, transformers, or other interface circuitry, the incorporation of which is neither required nor desired within the context of the instant invention.

The forgoing limitations of prior art devices and methods have been overcome with the invention herein described, namely a device and method for operating a bipolar bulk vaporization or cutting device using the output of a general-purpose electrosurgical generator. Specifically, the bipolar device is connected via cabling using standard connectors to the monopolar outputs of the generator without adding resistors, capacitors, inductors, transformers or other interface circuitry distal to the generator.

Figure 3:
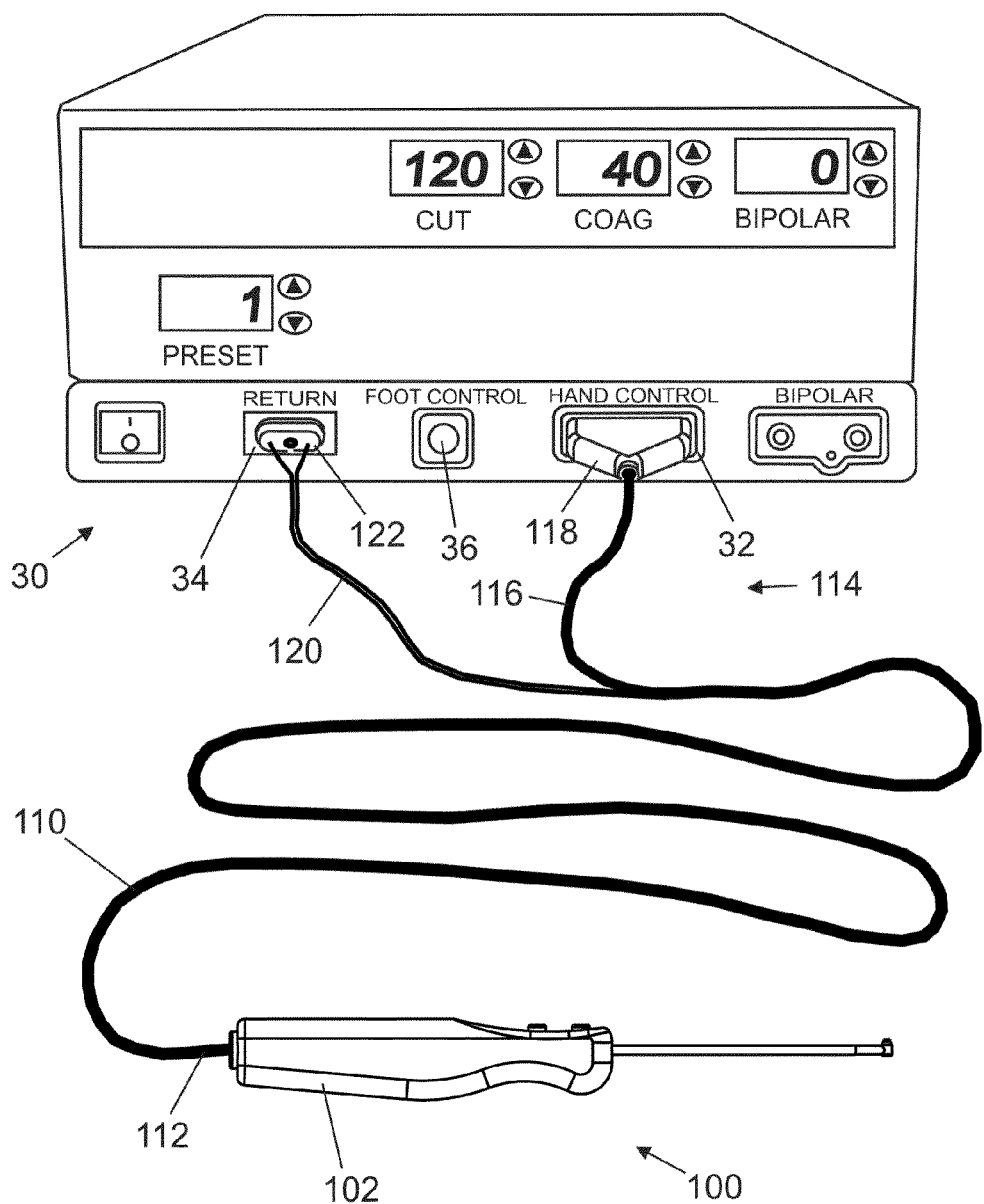
FIG. 3 depicts an electrosurgical system constructed in accordance with the principles of this invention.
Figure 4:
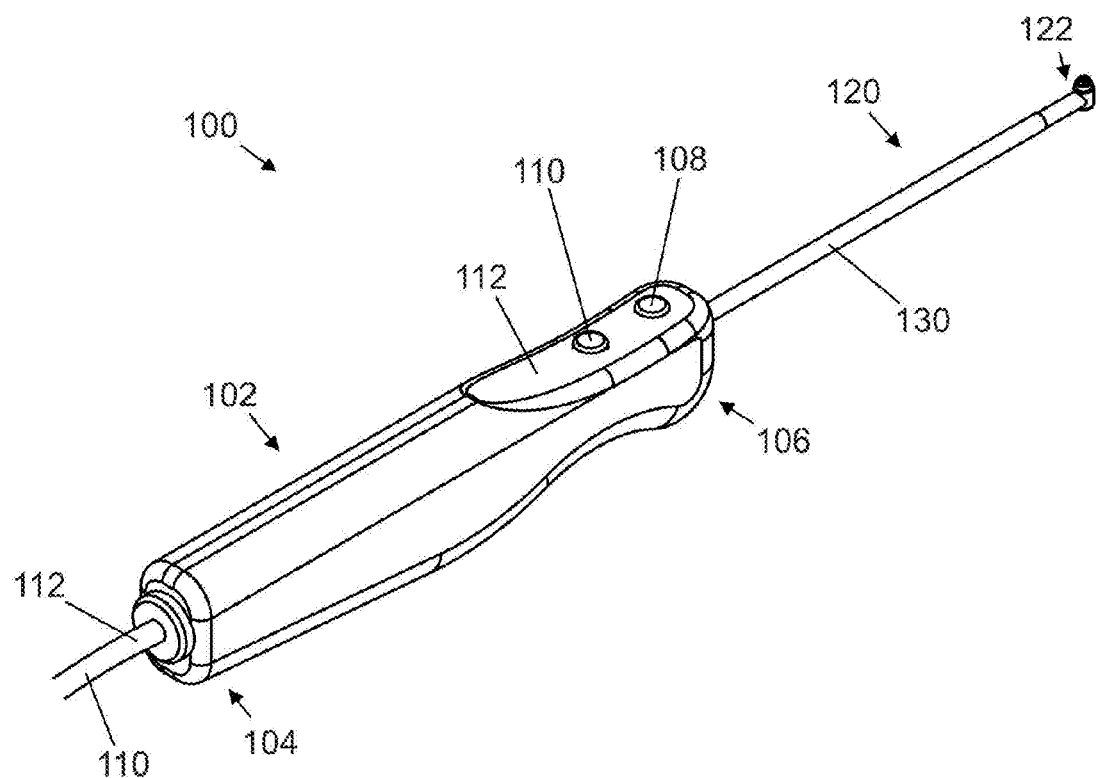
FIG. 4 is a perspective view of a bipolar electrosurgical device constructed in accordance with the principles of this invention.
Figure 5:
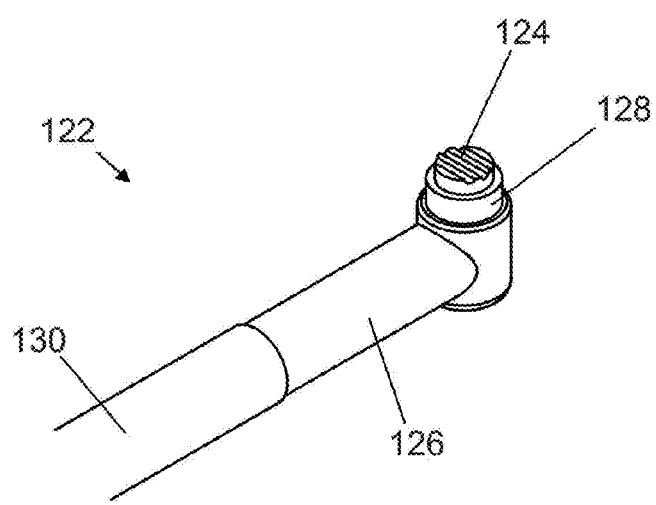
FIG. 5 is a perspective view of the distal portion of the objects of FIG. 4

FIG. 3 depicts a bipolar vaporization device 100 connected via cable 110 to a general-purpose generator, more particularly the return socket 34 and hand control socket 32 of the generator 30 in accordance with the principles of this invention. As best seen in FIGS. 4 and 5, bipolar device 100 has a proximal portion forming a handle 102, cable 110 passing from proximal end 104 of handle 102, and elongate distal portion 120 protruding from distal end 106 of handle 102. First activation button 108 and second activation button 110 are positioned on distal upper surface 112 of handle 102. Elongate distal portion 120 has at its distal end 122 an active electrode 124 and a return electrode 126 separated from each other by insulator 128. Dielectric coating 130 covers portions of elongate distal portion 120 proximal to return electrode 126.

Figure 6:
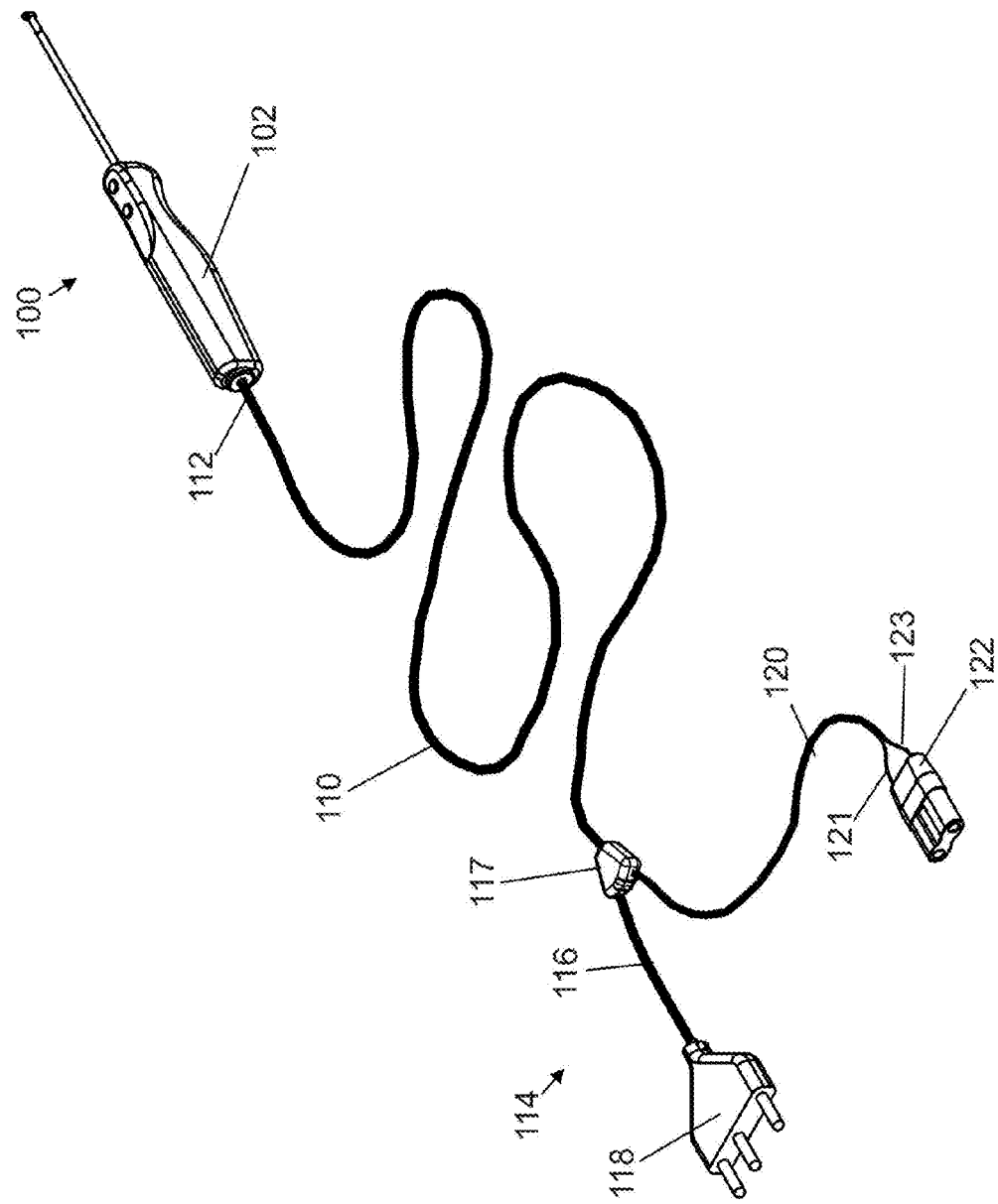
FIG. 6 depicts a cord and hand-controlled electrosurgical device constructed in accordance with the principles of this invention.

Referring now to FIG. 6 depicting device 100 and cable 110, distal end 112 of cable 110 is connected to circuitry within handle 102 of device 100. Proximal portion 114 of cable 110 divides into two portions connected at junction 117; first portion 116 having at its proximal end a three-pin connector 118 configured for connection to the return socket 34 (FIG. 3) for hand-controlled monopolar devices, and second portion 120 having at its proximal end connector 122 configured for connection to the socket 34 for the monopolar return. First proximal portion 116 of cable 110 provides RF energy to active electrode 124 via means within handle 102, and provides communication with first and second activation buttons 108 and 110 respectively such that depressing first button 108 causes RF energy of a first waveform and preset power level to be supplied to active electrode 124, and depressing second button 110 causes RF energy of a second waveform and preset power level to be supplied to active electrode 124. Second proximal portion 120 of cable 110 is connected via means within handle 102 to return electrode 126. Wires 121 and 123 are electrically isolated in second proximal portion 120, within junction 117, and throughout the length of cable 110, being electrically connected at handle 102 by means within handle 102. The electrically conductive paths of which wires 121 and 123 are the proximal ends need not be continuous wires throughout the entirety of cable 110, but may be composed of discreet wire portions connected by junctions or other conductive means.

In other contemplated embodiments, the return path from the return electrode may be a cable separate from cable 110, either removably or permanently affixed to cable 110, or unattached. Such devices and systems are considered to be embodiments of the present invention so long as the active electrode of the device is electrically connected to a monopolar output of the generator, and the device return electrode is electrically connected to the generator return.

Connector 122 (FIGS. 3, 6) is a standard single foil return connector like connector 821 (FIG. 2(a)). Using a return connector like 821 (FIG. 2(a)) is contemplated by the present invention provided that no external resistors, capacitors, inductors, transformers or other interface circuitry are used distal to the generator. Use of a single-foil connector 821 provides enhanced safety due to the internal return electrode monitoring unit of the generator, which continuously monitors the electrical continuity of the conductive path between receptacle 34 and the handpiece 102 (FIG. 3) which provide the return path during medical procedures. In some embodiments the connector 821 may be modified by electrically connecting conductors 825 of the connector 821 internally or immediately distal to connector 821 such that a single wire provides the return path for the device. In still other embodiments, the conductors 825 (121 and 123 in FIG. 6) may be connected distal to connector 122 but proximal to handle 102, for instance in junction 117. Such alternatives are contemplated by the present invention as long as no resistors, capacitors, inductors, transformers or other interface circuitry are added.

In preparation for use, connectors 118 and 122 (FIGS. 3,6) are connected to sockets 32 and 34 of generator 30 respectively. The monopolar power levels are set to appropriate levels, the "cut" value being the level of power of the first (cut) waveform delivered to the active electrode when first button 108 is depressed, and the "coag" value being the level of power of the second waveform delivered to the active electrode when second button 110 is depressed. Distal portion 120 of device 100 is inserted, for example, into a fluid filled cavity within the body of a patient. Active electrode 124 is positioned in contact with, or close proximity to tissue to be vaporized. First button 108 is depressed causing RF energy of the first (cut) waveform and power level to be delivered by generator 30 via cable 110 to active electrode 124 so as to vaporize the tissue, the energy returning to generator 110 via return electrode 126 and cable 110. If a bleeder is encountered active electrode 124 is positioned in contact with tissue in the region of the bleeder. Second button 110 is depressed causing RF energy of the second (coag) waveform and power level to be delivered by generator 30 via cable 110 to active electrode 124 so as to desiccate the tissue, the energy returning to generator 110 via return electrode 126 and cable 110.

Figure 7:
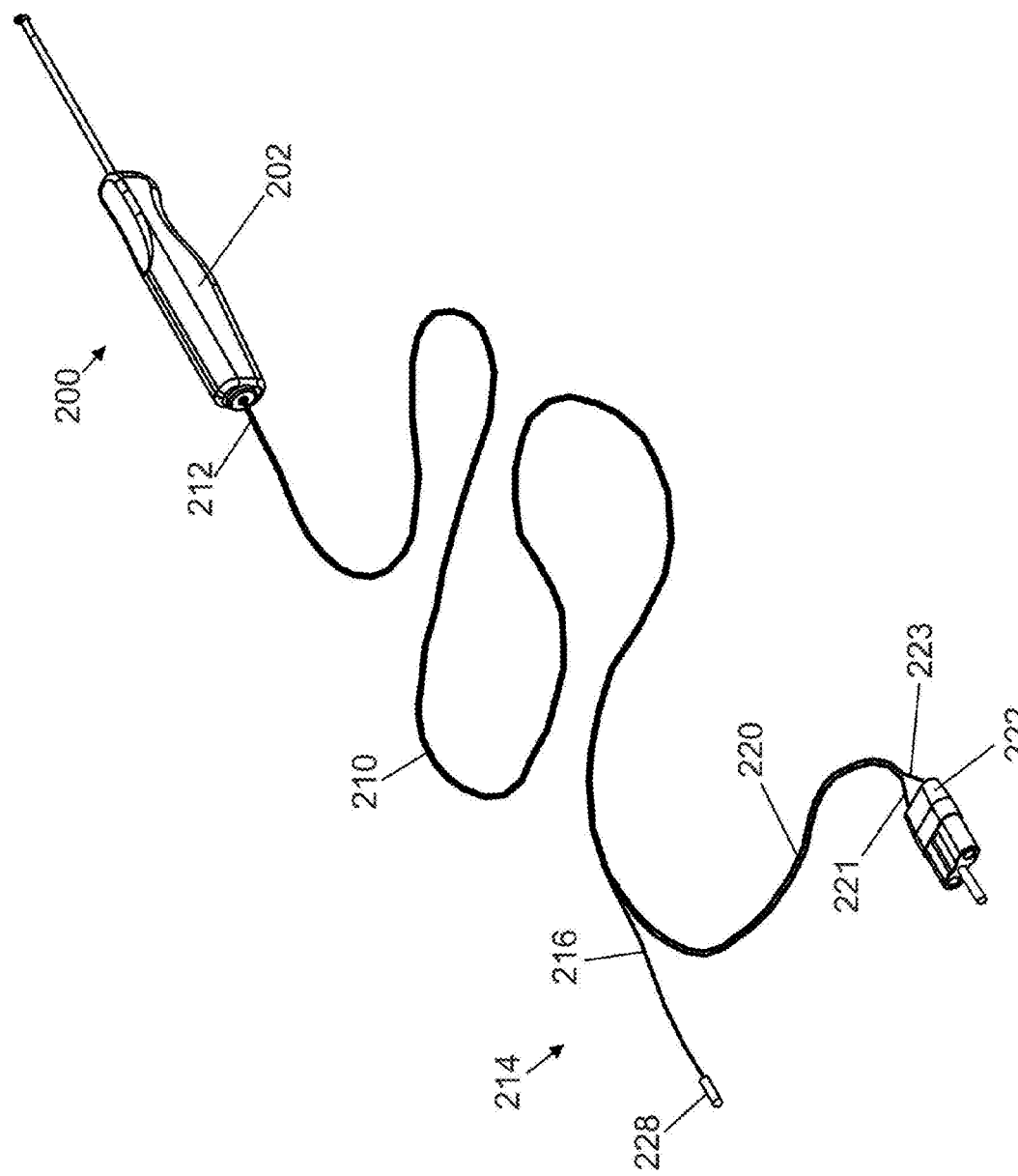
FIG. 7 depicts a cord and foot-controlled electrosurgical device constructed in accordance with the principles of this invention.

FIG. 7 depicts an alternate cabling embodiment in which device 200 is activated by a footswitch connected to electrosurgical generator 30. Distal end 212 of cable 210 is connected to circuitry within handle 202 of device 200. Proximal portion 214 of cable 210 divides into two portions; first portion 216 having at its proximal end single-pin connector 228 configured for connection to the socket 36 for foot-controlled monopolar devices, and second portion 220 having at its proximal end connector 222 configured for connection to the socket 34 for the monopolar return. First proximal portion 216 of cable 210 provides RF energy to the active electrode via means within handle 202. Second proximal portion 220 of cable 210 is connected via means within handle 202 to the return electrode. Operation of device 200 is identical to that of device 100 except that activation of device 200 is accomplished by depressing the appropriate foot pedals attached to generator 30. Connector 222 for connection to the Monopolar Return socket 34 is a "dual foil" configured connector like that depicted in FIG. 2(b). Wires 221 and 223 are electrically isolated in second proximal portion 220 and throughout the length of cable 210, being electrically connected at handle 202 by means within handle 202. The conductive paths of which wires 221 and 223 are the proximal ends need not be continuous wires throughout the entirety of cable 210, but may be composed of discreet wire portions connected by junctions or other conductive means. Whether the conductive paths are formed of continuous wires or of wire portions, junctions or other means, the resistance between the proximal ends of wires 221 and 223 has a value that is within the specified range of the return monitoring circuitry within the generator. No resistors, capacitors, inductors, transformers or other interface circuitry are used distal to the generator.

Figure 8:
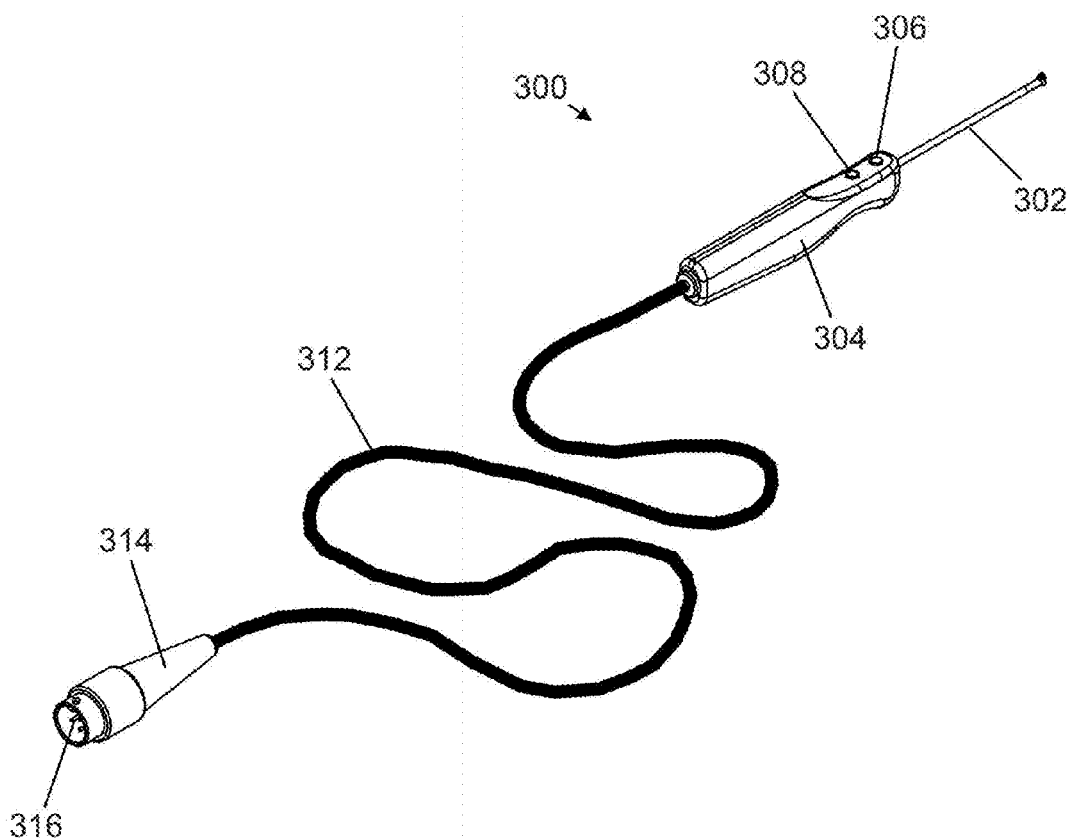
FIG. 8 depicts a prior art bipolar device used with a dedicated generator.
Figure 9:
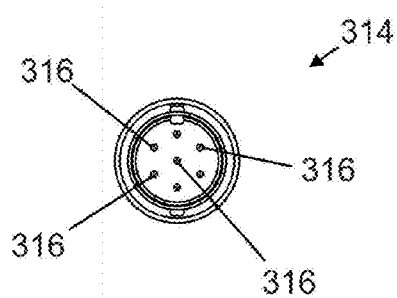
FIG. 9 is an axial view of the connector at the proximal end of the cable of bipolar device of FIG. 8.

FIGS. 8 and 9 depict a prior art bipolar electrosurgical device 300 constructed for use with a dedicated generator. Examples of this type of device include Arthrowands by Arthrocare, Inc. (Austin, Tex.), VAPR® Electrodes by Depuy/Mitek Inc. (Raynham, Mass.), and SERFAS Energy probes by Stryker, Inc. (San Jose, Calif.). Device 300 has an elongated distal portion 302 and a proximal portion 304 forming a handle having on its distal upper portion with first activation button 306 and second activation button 308. Cable 312 has at its distal end device 300 and at its proximal end connector 314 having multiple pins 316. Connector 314 is normally connected via a mating receptacle to a special purpose electrosurgical generator (not shown), pins 316 of connector 314 providing electrical connection to probe 300 via cable 312. The active and return electrodes are connected to the generator via pins 316, as well as activation buttons 306 and 308. Additionally, via pins 316 circuitry within the dedicated generator may identify the device attached to it so as to preset the generator to suitable power parameters for the particular device type, and limit the maximum power that may be applied, as well as other power characteristics.

In some instances, it may be desirable to use a prior art bipolar devices designed for use with a dedicated special purpose generator, but powered instead by a general-purpose generator. For instance, one may easily envision procedure scheduling issues when multiple operating rooms are in use simultaneously and there are insufficient special-purpose generators. Also, refurbishing of single-use medical devices has made these prior art bipolar devices available at a reduced cost. Using such devices with multi-purpose electrosurgical generators already available in every operating room leads to further savings since a special purpose generator need not be purchased for use with the refurbished devices.

Figure 10:
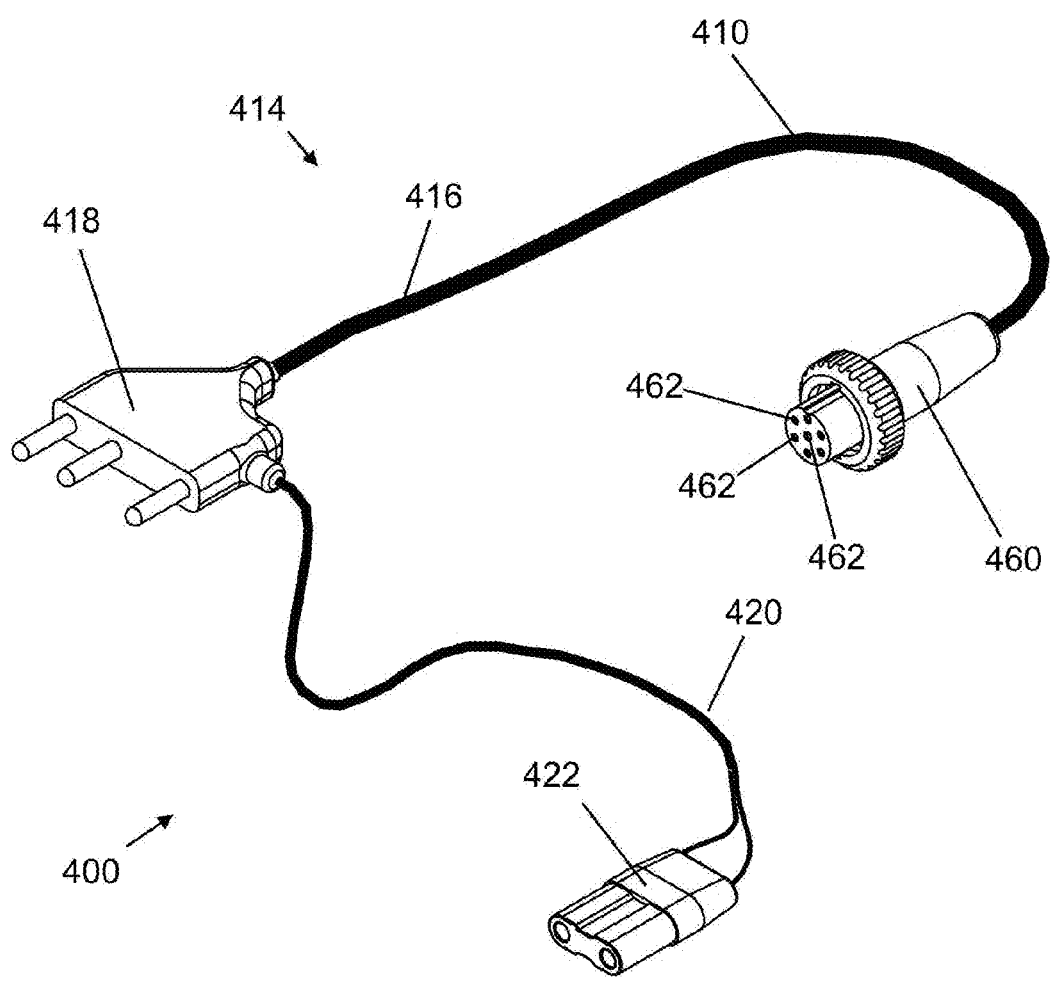
FIG. 10 depicts an alternate embodiment of the invention herein disclosed which is an adaptor for connecting the bipolar device of FIG. 8 to the monopolar outputs of a standard electrosurgical generator.

Accordingly, FIG. 10 depicts an adaptor 400 for connecting prior art bipolar RF devices that are designed for a dedicated special-purpose generator instead to a general-purpose generator. The proximal portion of adaptor 400 is constructed identically to cable 110 (FIG. 6). Proximal portion 416 of cable 410 divides into two portions; first portion 416 having at its proximal end a three-pin connector 418 configured for connection to the socket 32 for hand-controlled monopolar devices, and second portion 420 having at its proximal end connector 422 configured for connection to the socket 34 for the monopolar return. Adaptor cable 410 has at its distal end connector 460 configured to mate with connector 314 of prior art device 300 (FIGS. 8 and 9). Connector 460 is configured such that the pin or pins 316 of connector 314 which supplies power to the active electrode of device 300 is connected via first proximal portion 416 of adaptor cord 410 to three-pin connector 418 in a manner so that upon activation of the generator, power is conducted to the active electrode. In the same manner, pins 316 of connector 314 which cause generator activation when first button 306 or second button 308 (FIG. 8) is depressed may be connected to the three-pin connector 418 so that buttons 306 and 308 activate the Cut or Coag function of the general-purpose generator when depressed, though in some existing devices other non-standard hand-activation protocols may be used and hand-control of the device may be impossible. In these cases, it would necessary to control the device via foot controls attached to the generator. The return electrode is similarly connected via a pin or pins 316 of connector 314, connector 460 and second proximal portion 420 to return connector 422. Pins 316 related to identification of the device by the special purpose generator are not used since the general-purpose generator has no corresponding function.

Figure 11:
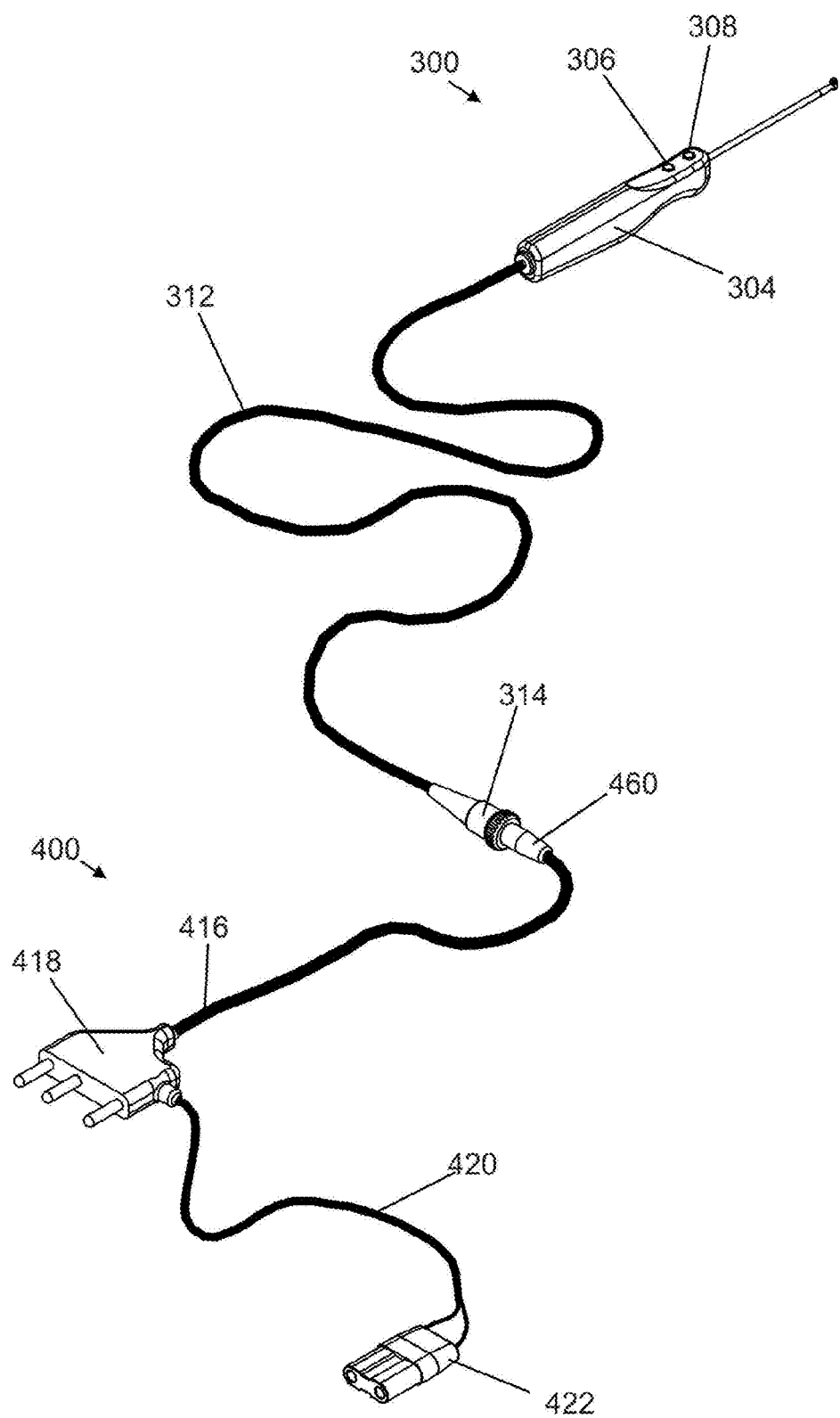
FIG. 11 depicts an assembly of the prior art bipolar device of FIG. 8 and the adaptor of FIG. 10.

FIG. 11 depicts probe 300 and adaptor 400 removably assembled in accordance with the principles of this invention, connector 314 and connector 460 being removably connected to each other. The assembly depicted is functionally equivalent to device 100 (FIG. 6) and is connected to a general-purpose generator as depicted in FIG. 3. Operation of device 300 with adaptor 400 is the same as operation of device 100.

It should be noted that while using device 300 with adaptor 400 allows use of the device with a general-purpose generator, it affects no other non-electrical aspect of the probe's operation. Specifically, if probe 300 has aspiration or irrigation or both, these features of the probe and its operation are unaffected.

Indeed, while probe 100 and probe 200 are depicted without either aspiration or irrigation, either may have either or both of these features. Because these bipolar probes will still be connected to the monopolar connectors of a general-purpose generator, they are still considered to be embodiments contemplated by the present invention. Accordingly, bipolar devices constructed in accordance with the principles of this invention may be used for tissue cutting or vaporization in fluid filled cavities, either naturally occurring or created, or in dry or semi-dry environments where external irrigants are supplied to the device.

Figure 12:
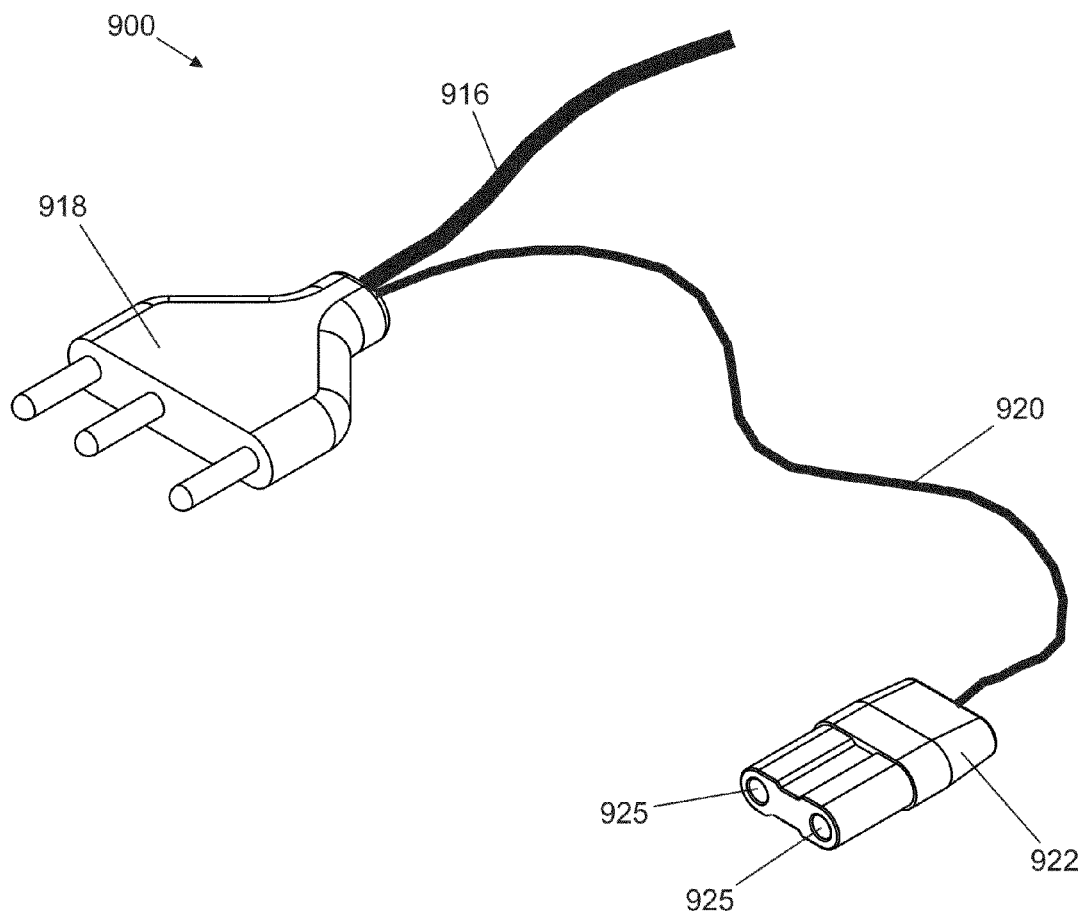
FIG. 12 depicts the proximal cable portion of an alternate embodiment.

FIG. 12 depicts the proximal portion of the cable assembly 900 of a bipolar device constructed in accordance with the principles of this invention. Although the distal portions are not shown, they are identical to those of ablator 100 (FIGS. 3 through 6). Second proximal portion 920 is connected at its proximal end to the distal portion of three-pin connector 918 adjacent to the proximal end of first proximal portion 916 of cable 910, and at its distal end to return connector 922. Unlike previous embodiments, second portion 920 is a single wire, conductors 925 of return connector 922 being electrically connected, either internally to connector 922, or externally adjacent to the distal end of connector 922. Proximal assembly 900 together with its bipolar device function in the same manner as device 100. Because conductors 925 of connector 922 are electrically connected at connector 922, monitoring of the return path integrity by the generator is not present. Failure of the return path will cause the ablation device to become inoperable, however, the generator will not register an alarm.

Figure 13:
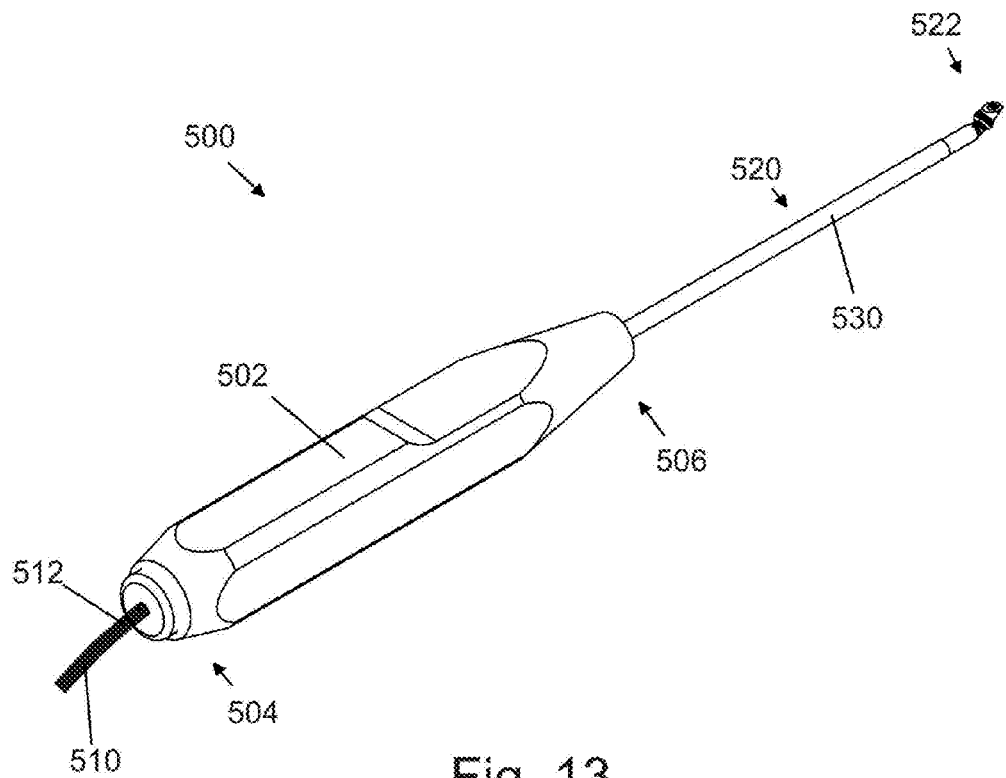
FIG. 13 depicts a bipolar device used for performance evaluation.
Figure 14:
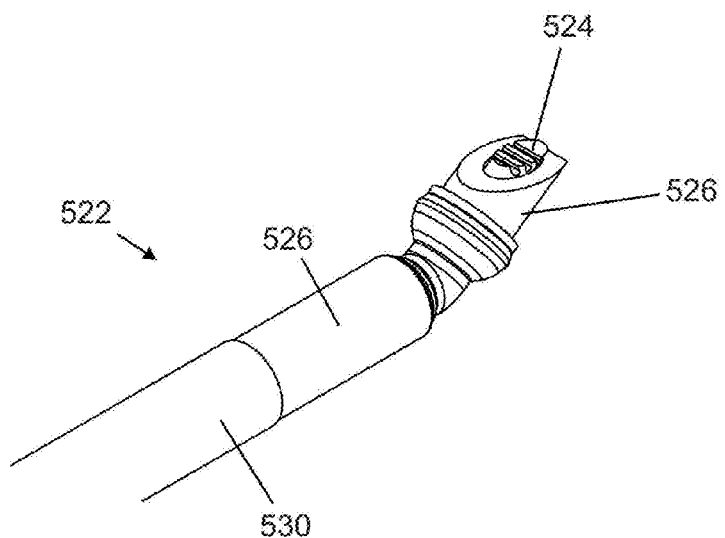
FIG. 14 depicts the distal portion of the device of FIG. 12.
Figure 15:
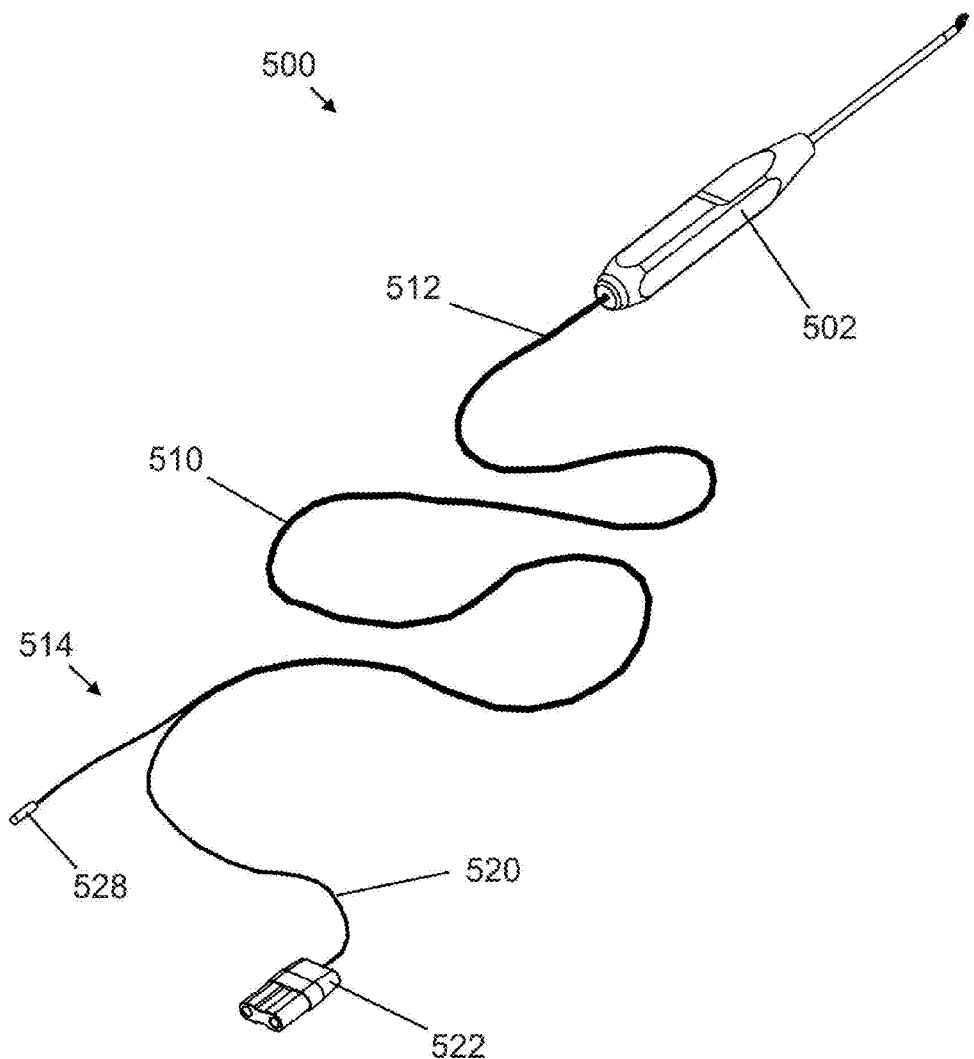
FIG. 15 depicts the bipolar device of FIG. 12 with a cable constructed in accordance with the principles of this invention for connection to the foot controlled monopolar outputs of a standard electrosurgical generator.

FIGS. 13 through 15 depict a foot-pedal controlled bipolar device 500 constructed in accordance with the principles of this invention. Device 500 has a proximal portion forming a handle 502 and a distal portion 520 having a distal end 522 with an active electrode 524 surrounded by an insulator 526, and a return electrode 526. Proximal to return electrode 526, dielectric coating 530 covers part of the distal portion 520. Cable 510 is identical in all aspects to cable 10 of foot-pedal controlled device 200 depicted in FIG. 7.

Device 500 was operated in a bipolar mode in accordance with the principles of this invention, and also in a monopolar mode, that is, using a remotely located return pad rather than the return on the device, to determine the effect of the return electrode position on device performance. Comparison tests were performed using a Bovie IDS-300 general-purpose electrosurgical generator. Tissue submerged in standard 0.9% saline solution was vaporized and the tissue removal rates at two power setting determined. The results show equivalent performance for the bipolar and monopolar operation.

In the embodiments herein described, devices are depicted as bipolar arthroscopy ablators. This is meant for illustration only and not meant in any way to limit the scope of the invention. The principles of the invention may be advantageously applied to any bipolar device used primarily for cutting or bulk vaporization of tissue in various fields such as, for example, laparoscopy, general surgery, urology, veterinary, treating tumors and others. Similarly, the principles of the invention may be advantageously applied in environment with conductive and no conductive fluids as well as with bodily fluids and semi dry fields.

More specifically, the instant invention may be used for any bipolar device in which the return electrode is mounted in a fixed position in close proximity to the active electrode on the device such that the associated spacial relationship is maintained during movement of the device. This is in contrast to devices marketed as "bipolar" because they do not use a conventional return pad, but rather use another return path at the surgical site. For instance, the Olympus Button Plasma Vaporization Electrode by Gyms ACMI (Southborough, Mass.), and SalineTrode products by ProSurg, Incorporated (San Jose, Calif.), intended for urological procedures employing a resectoscope, use the resectoscope body as a return electrode, the scope body being electrically connected via cabling to the return receptacle of the generator. In such devices the spatial relationship between the active electrode and return electrode is not fixed since the return electrode is not on the ablation/cutting device, but rather on the resectoscope that manipulates the device. Devices such as these are outside the scope of this invention.

The invention herein disclosed may be advantageously applied to urological devices that have a return electrode in close fixed proximity to the active electrode. Indeed, all bipolar devices for tissue vaporization and/or cutting regardless of the surgical specialty may realize the decreased cost and improved performance benefits of this invention.

Figure 16:
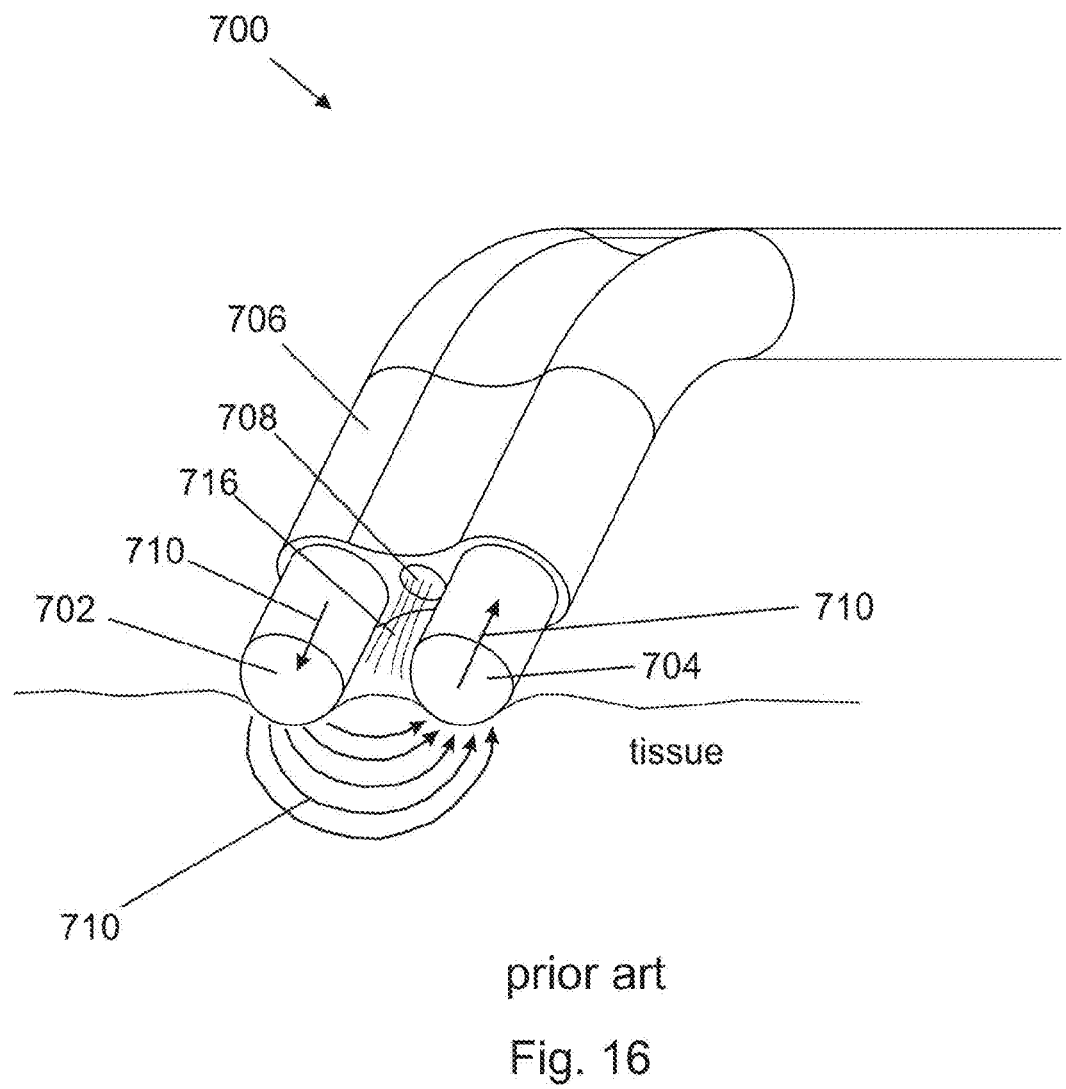
FIG. 16 depicts the distal portion of a prior art bipolar surface coagulating device that may be powered by the monopolar outputs of a standard general-purpose electrosurgical generator in accordance with the principles of this invention.

The instant invention may also be applied to bipolar devices for surface coagulation. The distal portion of one such prior art device 700 is depicted in FIG. 16. A pair of symmetrically identical electrodes 702 and 704 have hemispherical distal surfaces, and have a fixed separation maintained by dielectric element 706. Optionally, an irrigation port is positioned in proximity to the distal portions of electrodes 702 and 704. Electrode 702 is connected by means within the device handle (not shown) and cabling configured as previously taught herein to the monopolar output of a standard general-purpose electrosurgical generator. Electrode 704 is connected in the same manner to a monopolar return receptacle of the generator. During use, prior to activation, electrodes 702 and 704 are brought into firm contact with the tissue and/or irrigant and/or body fluids to be coagulated. When device 700 is activated, current 710 flows from portions of electrode 702, through the tissue to portions of electrode 704 in contact with the tissue so as to desiccate tissue in the current path. If irrigant 716 is supplied to the site in vicinity of the electrode distal ends, the conductive irrigant 716 may be part of the conductive path between electrodes 702 and 704. Device 700 is traversed across the surface of the tissue to be coagulated in a manner that "paints" the region. Slower traverse rates and/or higher applied power result in deeper coagulation of the tissue.

A cable constructed in accordance with the principles of this invention for connecting a bipolar device to the monopolar active and return receptacles of a standard multipurpose electrosurgical generator uses a standard connector currently in use for either hand or foot control electrosurgical pencils, and a standard connector currently in use for dispersive electrodes; either single-foil or dual-foil configuration connectors may be used. No resistors, capacitors, transformers, inductors or other interface circuitry are incorporated in the cable or connectors distal to the electrosurgical generator. In preferred embodiments, the two wires connected to the return connector form the proximal ends of two discreet electrically isolated conductive paths extending to the distal end of the cable at the device where they are electrically connected to the device return electrode and thereby to each other. Each conductive path may be a continuous wire, or may be discreet wire segments joined by connectors or other connecting means. In other embodiments, the wires of the return connector are connected to each other (shorted) immediately distal to, or within the connector, and a single conductive path connects the return connector of the generator to the return electrode of the bipolar device. In still other embodiments, the wires of the return connector may be electrically connected to each other at another location distal to the connector but proximal to the bipolar device such that the return from the device has a distal portion with a single conductive path, and a proximal portion with two discreet paths electrically isolated through the portion.

Any cable having a proximal portion for connecting to the standard monopolar receptacles of a general-purpose electrosurgical generator and a distal portion for connecting to a bipolar electrosurgical device and which does not include any resistors, capacitors, inductors, transformers or other interface circuitry is contemplated by the present invention.

INDUSTRIAL APPLICABILITY

The cable assemblies of the instant invention are of a simple construction, suitable for use with a wide array of electrosurgical components and adaptable to wide range of devices in an array of diverse environments so as to address a host of ablation needs. Thus, present invention maximizes efficiency and adaptability while minimizing manufacturing costs and device profile.

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Such other advantages and features will become apparent from the claims filed hereafter, with the scope of such claims to be determined by their reasonable equivalents, as would be understood by those skilled in the art. Thus, the invention is defined not by the above description, but by the following claims and their equivalents.

What is claimed:

1. A cable assembly for connecting a bipolar electrosurgical device to monopolar active and monopolar return receptacles of a conventional multipurpose electrosurgical generator, said assembly consisting of:
   a. a first conductive path having a distal end configured for direct connection to a first electrode of said bipolar electrosurgical device and a proximal end comprising a first connector configured for direct connection to a monopolar active receptacle of said generator; and
   b. a second conductive path having a distal end configured for direct connection to a second electrode of said bipolar device and a proximal end comprising a second connector configured for direct connection to a monopolar return receptacle of said multipurpose electrosurgical generator;
   wherein said cable assembly is free from discrete electronic components selected from the group consisting of resistors, capacitors, inductors, transformers, and other interfacing circuitry;
   further wherein said cable assembly permits said bipolar electrosurgical device to be operated in multiple modes and using standard control methods.

2. The cable assembly of claim 1, wherein said first connector is a standard three-pin connector conventional to a standard hand-controlled electrosurgical pencil.

3. The cable assembly of claim 1, wherein said first connector is a standard single terminal conventional to a standard foot-controlled electrosurgical pencil.

4. The cable assembly of claim 1, wherein said second connector is a standard return connector conventional to a single-foil (solid) dispersive (return) pad.

5. The cable assembly of claim 1, wherein said second connector is a standard return connector conventional to a dual-foil (split) dispersive (return) pad.

6. The cable assembly of claim 1, wherein said second conductive path comprises a pair of parallel conductive paths electrically connected at their respective distal ends.

7. The cable assembly of claim 1, wherein said second conductive path comprises a proximal portion comprising a pair of parallel conductive paths, and a distal portion comprising a single conductive path.

8. The cable assembly of claim 1, wherein the distal ends of said first conductive path and said second conductive path converge into a single cable having a multi-pin connector at its distal end.

9. An electrosurgical system comprising:
   a. a bipolar electrosurgical device configured for cutting or vaporizing tissue, said bipolar device having a proximal portion forming a handle and an elongate distal portion having at its distal end a first electrode comprising a conductive active electrode and a second electrode comprising a conductive return electrode in close proximity to said active electrode; and
   b. a cable assembly having one end connected to said proximal portion of said bipolar electrosurgical device and a second end configured for connection to monopolar active and monopolar return receptacles of a conventional multipurpose electrosurgical generator, said assembly comprising:
      i. a first conductive path having a distal end in communication with said first electrode of said bipolar electrosurgical device and a proximal end comprising a first connector configured for connection to a monopolar active receptacle of said generator; and
      ii. a second conductive path having a distal end in communication with said second electrode of said bipolar device and a proximal end comprising a second connector configured for direct connection to a monopolar return receptacle of said multipurpose electrosurgical generator;
   wherein said cable assembly is free from discrete electronic components selected from the group consisting of resistors, capacitors, inductors, transformers, and other interfacing circuitry;
   further wherein said cable assembly permits said bipolar electrosurgical device to be operated in multiple modes and using standard control methods.

10. The electrosurgical system of claim 9, wherein said first and said second electrodes of said bipolar electrosurgical device comprise a bipolar pair having smooth surfaces configured for coagulation.

11. The electrosurgical system of claim 9, wherein said bipolar electrosurgical device is a radiofrequency device.

12. The electrosurgical system of claim 9, wherein said bipolar electrosurgical device comprises a bipolar arthroscopy ablator.

13. The electrosurgical system of claim 11, wherein said bipolar electrosurgical device comprises a bipolar coagulating forceps.

\* \* \* \* \*